US009989532B2

(12) United States Patent
Monroe et al.

(10) Patent No.: US 9,989,532 B2
(45) Date of Patent: Jun. 5, 2018

(54) METHODS AND COMPOSITIONS FOR DETECTING COAGULATION INHIBITORS

(71) Applicant: The University of North Carolina at Chapel Hill, Chapel Hill, NC (US)

(72) Inventors: Dougald Monroe, Carrboro, NC (US); Jen-Yea Chang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 170 days.

(21) Appl. No.: 14/906,620

(22) PCT Filed: Jul. 24, 2014

(86) PCT No.: PCT/US2014/047974
§ 371 (c)(1),
(2) Date: Jan. 21, 2016

(87) PCT Pub. No.: WO2015/013495
PCT Pub. Date: Jan. 29, 2015

(65) Prior Publication Data
US 2016/0187338 A1 Jun. 30, 2016

Related U.S. Application Data

(60) Provisional application No. 61/859,148, filed on Jul. 26, 2013.

(51) Int. Cl.
| | |
|---|---|
| G01N 33/573 | (2006.01) |
| G01N 33/50 | (2006.01) |
| G01N 33/86 | (2006.01) |
| A61K 38/17 | (2006.01) |
| A61K 38/48 | (2006.01) |
| A61K 38/57 | (2006.01) |

(52) U.S. Cl.
CPC ....... *G01N 33/573* (2013.01); *A61K 38/1722* (2013.01); *A61K 38/4833* (2013.01); *A61K 38/4846* (2013.01); *G01N 33/502* (2013.01); *G01N 33/86* (2013.01); *A61K 38/57* (2013.01); *C12Y 304/21005* (2013.01); *C12Y 304/21006* (2013.01); *G01N 2333/96444* (2013.01); *G01N 2333/96463* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,192,689 A * | 3/1993 | Hemker | C12Q 1/56 435/13 |
| 8,343,730 B2 * | 1/2013 | Giesen | C12Q 1/56 435/13 |
| 2009/0148845 A1 * | 6/2009 | Berry | C12Q 1/37 435/6.1 |
| 2012/0208225 A1 * | 8/2012 | Berry | C07K 5/0812 435/24 |

OTHER PUBLICATIONS

Boisset et al. "Image Processing of Proteinase- and Methylamine-transformed Human α2-Macroglobulin" *The Journal of Biological Chemistry* 264(20):12046-12052 (1989).
Ikeda et al. "Biochemical Markers of Coagulation Activation in Mitral Stenosis, Atrial Fibrillation, and Cardiomyopathy" *Clinical Cardiology* 20:7-10 (1997).
International Search Report and the Written Opinion of the International Searching Authority corresponding to International Patent Application No. PCT/US2014/047974 (9 pages) (dated Nov. 20, 2014).
Meijers et al. "Inhibition of Human Blood Coagulation Factor Xa by α$_2$-Macroglobulin" *Biochemistry* 26:5932-5937 (1987).
Girgis et al. "Population Pharmacokinetics and Pharmacodynamics of Rivaroxaban in Patients with Non-valvular Atrial Fibrillation: Results from ROCKET AF" *The Journal of Clinical Pharmacology* 54(8):917-927 (2014).
Gnoth et al. "In Vitro and In Vivo P-Glycoprotein Transport Characteristics of Rivaroxaban" *The Journal of Pharmacology and Experimental Therapeutics* 338(1):372-380 (2011).
International Preliminary Report on Patentability corresponding to International Patent Application No. PCT/US2014/047974 (7 pages) (dated Feb. 4, 2016).
Johnson & Johnson Pharmaceutical Research & Development L.L.C. "Rivaroxaban for the Prophylaxis of Deep Vein Thrombosis (DVT) and Pulmonary Embolism (PE) in Patients Undergoing Hip or Knee Replacement Surgery" *Advisory Committee Briefing Book* (274 pages) (dated Feb. 12, 2009).
Rehman et al. "Alpha-2-Macroglobulin: A Physiological Guardian" *Journal of Cellular Physiology* 228:1665-1675 (2013).
Reilly et al. "The Effect of Dabigatran Plasma Concentrations and Patient Characteristics on the Frequency of Ischemic Stroke and Major Bleeding in Atrial Fibrillation Patients: The RE-LY Trial (Randomized Evaluation of Long-Term Anticoagulation Therapy" *Journal of the American College of Cardiology* 63(4):321-328 (2014).

(Continued)

*Primary Examiner* — Thane Underdahl
(74) *Attorney, Agent, or Firm* — Myers Bigel, P.A.

(57) ABSTRACT

The present invention provides a method of identifying a coagulation inhibitor in a sample, comprising: a) contacting a first portion of the sample with a substrate and thrombin; b) contacting a second portion of the sample with a substrate and a2M-thrombin (thrombin caged in alpha-2-macroglobulin); c) contacting a third portion of the sample with a substrate and coagulation factor Xa; d) contacting a fourth portion of the sample with a substrate and a2M-Xa (factor Xa caged in alpha-2-macroglobulin); and e) assaying for cleavage of the substrate in (a), (b), (c) and (d) above, wherein cleavage of the substrate in (b) and (d) and no cleavage in (a) and (c) identifies heparin in the sample; cleavage of the substrate in (a), (b) and (d) and no cleavage in (c) identifies low molecular weight heparin in the sample; cleavage of the substrate in (a) and (b) and no cleavage in (c) and (d) identifies rivaroxaban in the sample, and cleavage of the substrate in (c) and (d) and no cleavage in (a) and (b) identifies dabigatran in the sample.

2 Claims, 7 Drawing Sheets

(56) References Cited

OTHER PUBLICATIONS

Stangier et al. "Pharmacology, Pharmacokinetics, and Pharmacodynamics of Dabigatran Etexilate, an Oral Direct Thrombin Inhibitor" *Clinical and Applied Thrombosis/Hemostasis* 15(1S):09S-16S (2009).

Van Der Graaf et al. "Interaction of Human Plasma Kallikrein and Its Light Chain with $\alpha_2$-Macroglobulin" *Biochemistry* 23:1760-1766 (1984).

Van Ryn et al. "Dabigatran etexilate—a novel, reversible, oral direct thrombin inhibitor: Interpretation of coagulation assays and reversal of anticoagulant activity" *Thrombosis and Haemostasis* 103:1116-1127 (2010).

Weinz et al. "Pharmacokinetics of BAY 59/7939—an oral, direct Factor Xa inhibitor—in rats and dogs" *Xenobiotica* 35(9):891-910 (2005).

* cited by examiner

METHODS AND COMPOSITIONS FOR DETECTING COAGULATION INHIBITORS

STATEMENT OF PRIORITY

This application is a 35 U.S.C. § 371 national phase application of International Application Serial No. PCT/US2014/047974, filed Jul. 24, 2014, which claims the benefit, under 35 U.S.C. § 119(e), of U.S. Provisional Application Ser. No. 61/859,148, filed Jul. 26, 2013, the entire contents of each of which are incorporated by reference herein.

FIELD OF THE INVENTION

The present invention is directed to methods and compositions for detecting and/or identifying coagulation inhibitors in a sample. The present invention is also directed to methods and compositions for reducing the activity of an oral coagulation inhibitor in a subject.

BACKGROUND OF THE INVENTION

New oral anticoagulants are being introduced as improved therapies (over warfarin) in preventing thrombosis. One advantage is that no routine testing to monitor therapy is required for most patients. However, some patients with complications would benefit from a test for levels of these agents. Furthermore, a therapeutic to remove these new oral anticoagulants from the circulation of patients is not available and would be advantageous, for example, in allowing patients to stay on their oral anticoagulants until immediately prior to surgery and in allowing for patients on oral coagulants to be safely taken to emergency surgery.

The present invention overcomes these shortcomings in the art by providing methods and compositions for detecting a coagulation inhibitor in a sample, as well as for identifying the type and/or amount of coagulation inhibitor in the sample, even in the presence of other anticoagulant agents. Also provided is a therapeutic for administration to a patient taking an oral anticoagulant to rapidly bind the coagulation inhibitor and reduce its plasma concentrations, e.g., for emergency surgery and/or modulation of an adverse reaction to the anticoagulant.

SUMMARY OF THE INVENTION

In one aspect, the present invention provides a method of identifying a coagulation inhibitor in a sample, comprising: a) contacting a first portion of the sample with a substrate and thrombin; b) contacting a second portion of the sample with a substrate and a2M-thrombin (thrombin caged in alpha-2-macroglobulin); c) contacting a third portion of the sample with a substrate and factor Xa; d) contacting a fourth portion of the sample with a substrate and a2M-Xa (factor Xa caged in alpha-2-macroglobulin); and e) assaying for cleavage of the substrate in (a), (b), (c) and (d) above, wherein cleavage of the substrate in (b) and (d) and no cleavage in (a) and (c) identifies heparin in the sample; cleavage of the substrate in (a), (b) and (d) and no cleavage in (c) identifies low molecular weight heparin in the sample; cleavage of the substrate in (a) and (b) and no cleavage in (c) and (d) identifies rivaroxaban in the sample, and cleavage of the substrate in (c) and (d) and no cleavage in (a) and (b)) identifies dabigatran in the sample.

In further aspects, the method described above can further comprise the step of determining the amount of the coagulation inhibitor in the sample, comprising measuring the amount of cleavage of the substrate in (a), (b), (c) and/or (d) if cleavage was detected, wherein the amount of cleavage of the substrate allows for determination of the amount of the coagulation inhibitor in the sample.

In a further aspect, the present invention provides a method of reducing the activity of an oral coagulation inhibitor in the circulation of a subject who has taken an oral coagulation inhibitor, comprising, for example, administering to the subject a therapeutic amount of a2M-thrombin if the subject has taken an oral coagulation inhibitor that targets thrombin or administering to the subject a therapeutic amount of a2M-Xa if the subject has taken an oral coagulation inhibitor that targets factor Xa.

DETAILED DESCRIPTION OF THE INVENTION

Figure 1:
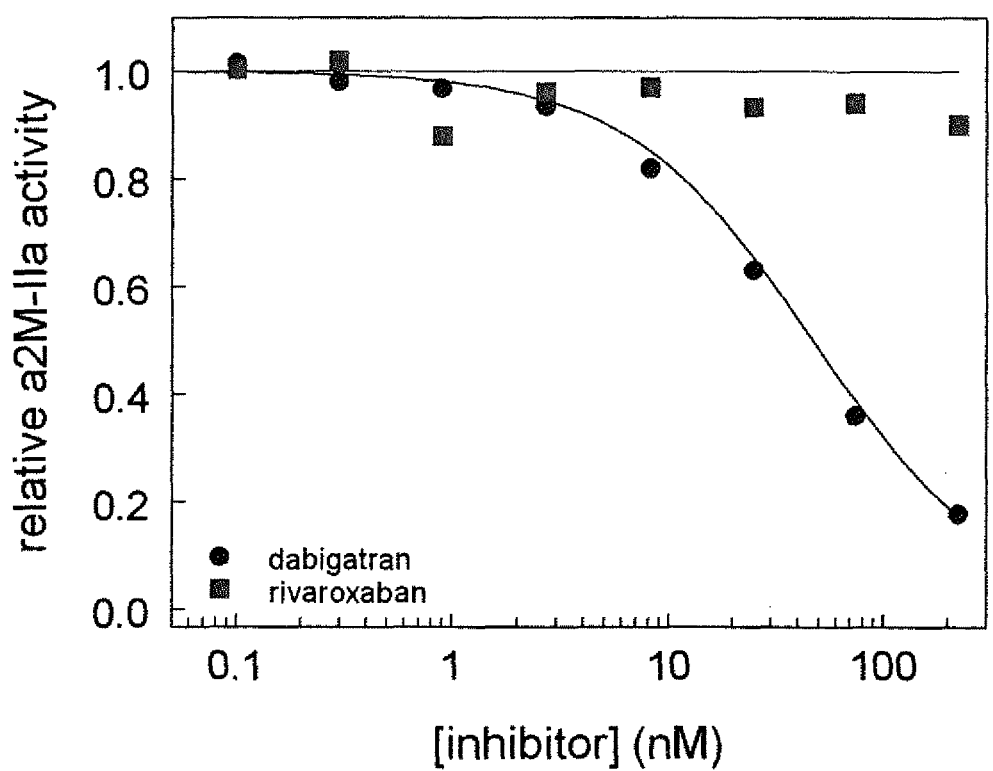
FIG. 1. Purified a2M-IIa was active since it would cleave a synthetic substrate. As expected, dabigatran bound to a2M-IIa and blocked substrate cleavage. Also as expected, rivaroxaban did not bind to a2M-IIa and did not block substrate cleavage.
Figure 2:
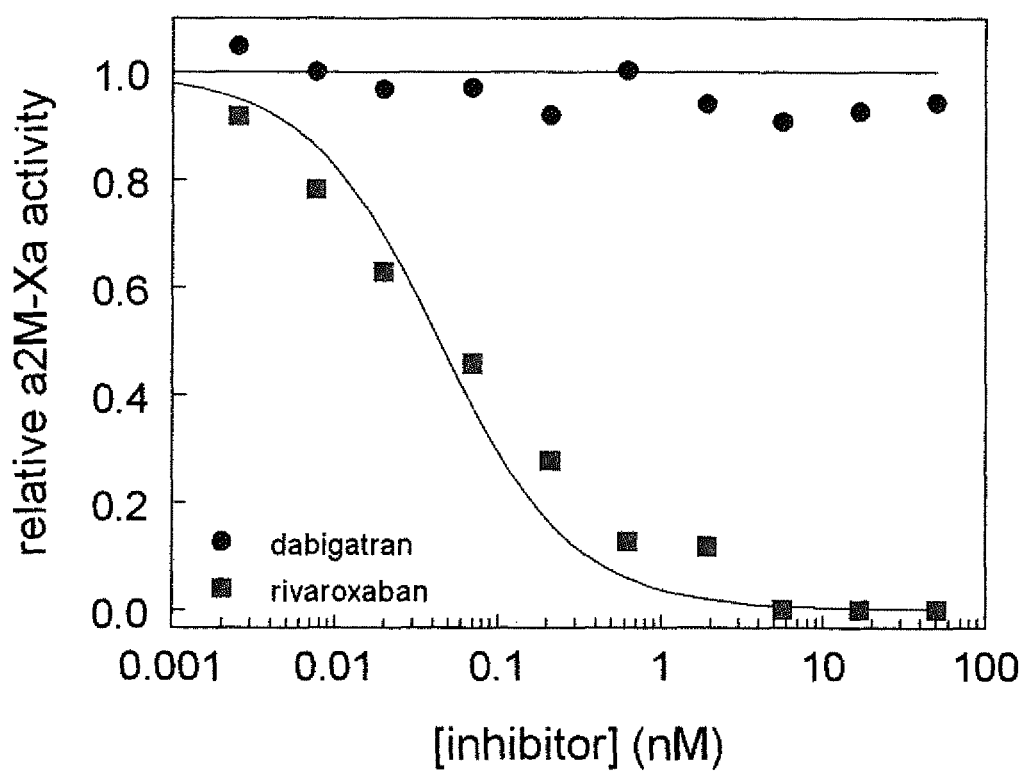
FIG. 2. Purified a2M-Xa was active since it would cleave a synthetic substrate. As expected, rivaroxaban bound to a2M-Xa and blocked substrate cleavage. Also as expected, dabigatran did not bind to a2M-Xa and did not block substrate cleavage.
Figure 3:
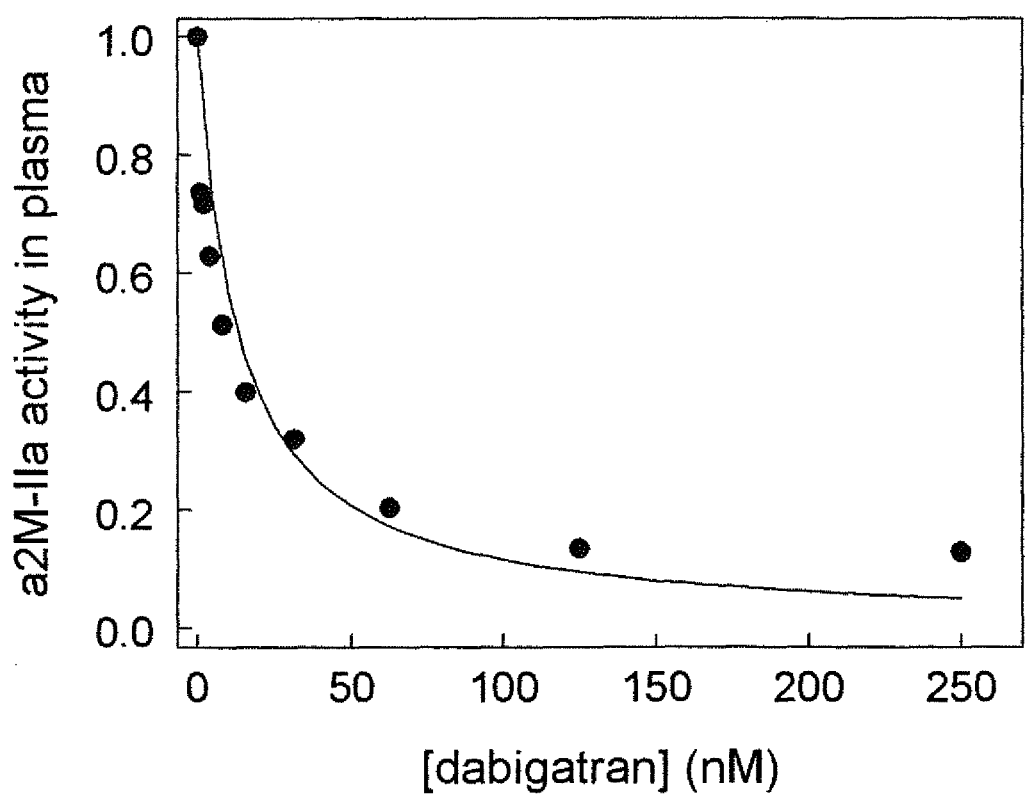
FIG. 3. a2M-IIa added to plasma was active as measured by synthetic substrate cleavage. So plasma inhibitors like antithrombin did not inactive a2M-IIa in plasma. Also, a2M-IIa in plasma could bind dabigatran as measured by blocking substrate cleavage.
Figure 4:
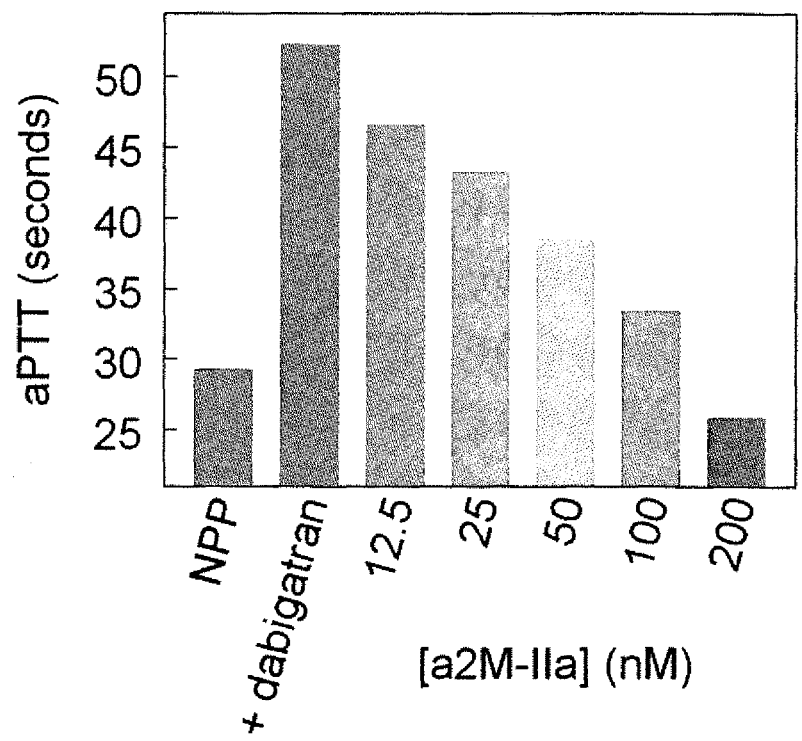
FIG. 4. When dabigatran was added to normal pooled plasma (NPP), the clotting time (aPTT) was slightly prolonged. Because a2M-IIa could bind to dabigatran, increasing doses of a2M-IIa added to NPP that contained a fixed dose of dabigatran could dose dependently shorten the clotting time to normal.
Figure 5:
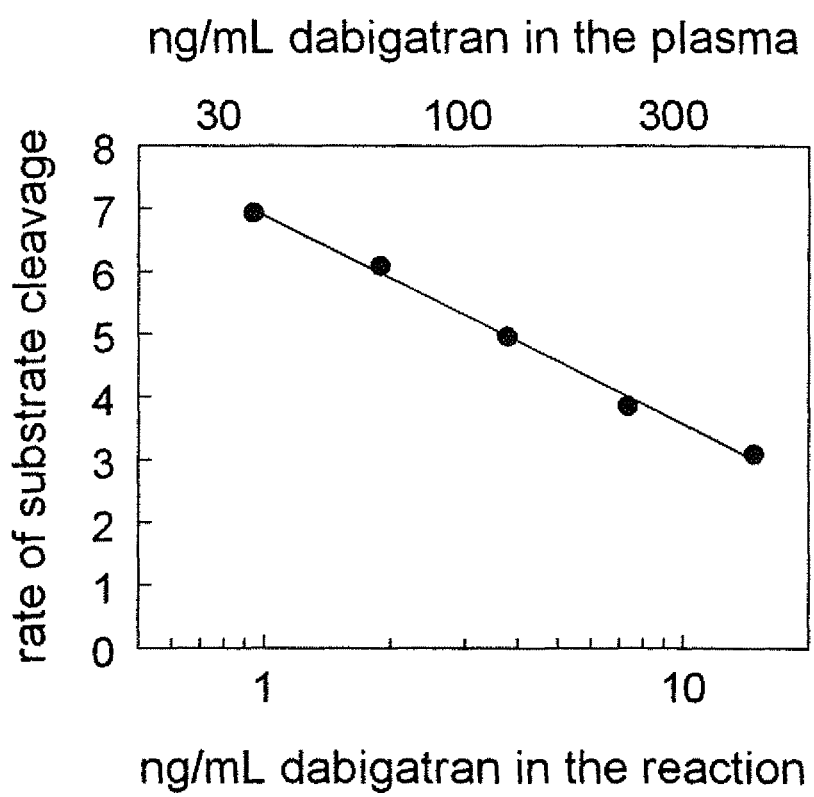
FIG. 5. Varying concentrations of dabigatran were added to plasma. The plasma was diluted 1:30 during addition to a fixed concentration of a2M-IIa. An equal volume of thrombin substrate (H-D-cyclohexylglycyl-alanyl-arginine para-nitroanilide) was added and cleavage of the substrate was measured at 405 nm. The rate of substrate cleavage was plotted against the concentration of dabigatran. The data was fit to a line; from this data fit, it is possible to determine the concentration of dabigatran in a test sample by comparing the rate of substrate cleavage to the standard curve.

As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

The present invention has been developed on the basis of the understanding that the target of coagulation inhibitors, for example, coagulation factor Xa and coagulation enzyme thrombin, can normally be inhibited by multiple different proteins in, for example, plasma. These inhibitors work by attacking these respective proteases, factor Xa and thrombin, at their active site, the portion of the protein that is responsible for activity. But because the active site of each of the many proteases is unique, different inhibitors are required for each protein.

The body has developed a universal inhibitor called alpha-2-macroglobulin (abbreviated a2M) (Rehman et al. "α-2-Macroglobulin: A Physiological Guardian" *J. Cell Physiol.* 228:1665-1675 (2013) doi: 10.1002/jcp.24266). a2M works by physically trapping the protease; based on crystal structure analysis, this has been described as a cage that the protease is trapped inside. Within this a2M cage, the protease (e.g., thrombin or factor Xa) is sequestered from any normal function. But, the active site is still intact and small molecules can still reach the active site even though large molecules, such as plasma inhibitors, are blocked. So synthetic substrates can still be cleaved by a2M caged factor Xa or thrombin and the small molecule inhibitors can still reduce substrate cleavage.

Thus, in some embodiments, the present invention provides a test method that has, for example, four elements and therefore four test conditions: thrombin, a2M-thrombin (a2M-IIa), factor Xa, and a2M-Xa. Substrate cleavage in the presence of test sample is measured for all four test conditions. The outcomes can be defined by a matrix (Table 1): heparin will inhibit substrate cleavage by thrombin and factor Xa but not a2M-thrombin or a2M-Xa; low molecular weight heparin will inhibit factor Xa but not thrombin or a2M-thrombin or a2M-Xa; rivaroxaban (sold as the oral drug XARELTO) will inhibit factor Xa and a2M-Xa but not thrombin or a2M-thrombin; and dabigatran (sold as the oral drug PRADAXA) will inhibit thrombin and a2M-thrombin but not factor Xa or a2M-Xa. Warfarin will inhibit none of the test reactions in this assay. Furthermore, for rivaroxaban and dabigatran, the degree of inhibition of substrate cleavage will be proportional to the amount of those agents present. These conclusions were established using a2M-Xa and a2M-thrombin prepared and tested as described herein.

Thus, in one aspect, the present invention provides a method of identifying a coagulation inhibitor in a sample, comprising: a) contacting a first portion of the sample with a substrate and thrombin; b) contacting a second portion of the sample with a substrate and a2M-thrombin (thrombin caged in alpha-2-macroglobulin); c) contacting a third portion of the sample with a substrate and factor Xa; d) contacting a fourth portion of the sample with a substrate and a2M-Xa (factor Xa caged in alpha-2-macroglobulin); and e) assaying for cleavage of the substrate in (a), (b), (c) and (d) above, wherein cleavage of the substrate in (b) and (d) and no cleavage in (a) and (c) identifies heparin in the sample; cleavage of the substrate in (a), (b) and (d) and no cleavage in (c) identifies low molecular weight heparin in the sample; cleavage of the substrate in (a) and (b) and no cleavage in (c) and (d) identifies rivaroxaban in the plasma sample, and cleavage of the substrate in (c) and (d) and no cleavage in (a) and (b)) identifies dabigatran in the sample (see e.g., Table 1).

It is understood that although the example above describes a test comprising four elements that establish at least four different test conditions, in some embodiments, the test or method of this invention can also comprise one, two or three elements to establish at least one, two or three test conditions in any combination. In some embodiments, the method can comprise more than four elements to establish more than four test conditions (e.g., at least five, six, seven, eight, nine, ten, etc.) in any combination.

In some embodiments, the methods described herein are for the purpose of inhibiting either thrombin or factor Xa activity rather than a specific agent so these methods will work against newly developed compounds that have the same activity.

A modification of this method could be used to assay for direct inhibitors of other coagulation proteases, nonlimiting examples of which include coagulation factor VIIa, coagulation factor IXa, coagulation factor XIa, coagulation factor XIIa, activated protein C (APC), kallekrein and plasmin, individually or in any combination. Thus, in some embodiments of this invention, small molecule inhibitors of factor IXa could be tested with a2M-IXa; small molecule inhibitors of factor VIIa could be tested with a2M-VIIa; small molecule inhibitors of factor XIa could be tested with a2M-XIa; small molecule inhibitors of factor XIIa could be tested with a2M-XIIa; small molecule inhibitors of activated protein C (APC) could be tested with a2M-APC; small molecule inhibitors of kallekrein could be tested with a2M-kallekrein; and/or small molecule inhibitors of plasmin could be tested with a2M-plasmin. In the respective assays, a substrate would be used that the particular enzyme would cleave. For example, a factor IXa substrate would be used for a2M-IXa, an APC substrate would be used for a2M-APC, etc., as such substrates are described herein and as are known in the art.

Further, since a2M-Xa and a2M-thrombin do not participate in coagulation reactions, they can be safely administered to a subject. Therapeutic levels of oral anticoagulants directed against factor Xa are in a range from about 70 nM (trough) to about 900 nM (peak) (Girgis et al. "Population pharmacokinetics and pharmacodynamics of rivaroxaban in patients with non-valvular atrial fibrillation: Results from ROCKET AF" *J Clin Pharmacol* 54:917-927 (2014). Therapeutic levels of oral anticoagulants directed against thrombin are in a range from about 80 nM (trough) to about 850 nM (peak) (Reilly et al. "The effect of dabigatran plasma concentration and patient characteristics on the frequency of ischemic stroke and major bleeding in atrial fibrillation patients: the RE=LY Trial (Randomized Evaluation of Long-Term Anticoagulation Therapy)" *J Am Coll Cardiol* 63:321-328 (2014). Administration of a2M-Xa or a2M-thrombin at levels higher than the plasma levels of factor Xa inhibitors or thrombin inhibitors, respectively, in the subject will result in rapid binding of the inhibitors, thereby reducing their plasma concentrations in the subject. In the present invention, a2M-Xa and a2M-IIa are prepared at sufficiently high concentrations that they could be administered to give therapeutic levels (e.g., moderately super-therapeutic levels). The goal is to administer a2M-Xa or a2M-IIa in an amount that is greater (e.g., 1% greater, 2% greater, 3% greater, 4% greater, 5% greater, 10% greater, 15% greater, 20% greater, 25% greater, 30% greater, 40% greater, 50% greater, 60% greater, 70% greater, 80% greater, 90% greater, 100% greater, 125% greater, 150% greater, 200% greater, 300% greater, etc.) than the plasma levels of the factor Xa inhibitors or thrombin inhibitors, respectively, to inactivate or inhibit the activity of the factor Xa inhibitors or thrombin inhibitors.

Currently there are no approved specific agents to reverse direct factor Xa or thrombin inhibitors. Since a2M-Xa and a2M-thrombin occur naturally in the body, there should be no risk of inhibitor development from administration at a higher dose (by analogy for example to NovoSeven which has been given at very high levels with no reported inhibitor development). Another advantage of a2M-Xa and a2M-thrombin as therapeutic agents is that protease complexes of alpha-2-macroglobluin occur naturally and the body has efficient mechanisms for clearing such complexes.

Dabigatran (sold as the oral drug PRADAXA) and rivaroxaban (sold as the oral drug XARELTO) are thrombin and factor Xa inhibitors, respectively, which are currently licensed in the US. The methods of this invention can also be applied to detect and/or quantify other thrombin inhibitors including, for example, argatraban, as well as any other thrombin inhibitor now known or later developed. The methods of this invention can also be applied to detect other factor Xa inhibitors including, for example, edoxaban, apixaban (sold under the brand name ELIQUIS), betrixaban and YM466, as well as any other factor Xa inhibitor now known or later developed, The methods of this invention can also be employed to detect any small molecule inhibitor of factor Xa now known or later developed.

Dabigatran directly inhibits both free and clot-bound thrombin. Dabigatran etexilate (a pro-drug) is rapidly converted (after oral administration and hepatic processing) to dabigatran, with peak plasma dabigatran concentrations recorded approximately 1.5 hours after oral ingestion. Once at steady state, dabigatran has a half-life of 14 to 17 hours. With oral treatment, bioavailability is 7.2%, and dabigatran is predominantly excreted in the feces.

Apixaban is a direct inhibitor of factor Xa (both within and outside the prothrombinase complex). When taken by mouth, apixaban has more than 50% bioavailability and reaches peak plasma concentration in 3 to 4 hours. The terminal half-life is 10 to 14 hours after repeated doses. Apixaban is metabolized in part by CYP3A4; it is partly eliminated by the kidneys (25%) and, to some extent, also processed via CYP-independent mechanisms in the liver.

Rivaroxaban, a direct factor Xa inhibitor, achieves maximum plasma levels approximately 3 hours after oral ingestion. Once at steady state, the terminal half-life is 4 to 9 hours (up to 12 hours in patients >75 years old). Very few significant drug-drug interactions are anticipated, and food does not affect absorption from the gastrointestinal tract; the oral bioavailability is more than 80%. Like apixaban, rivaroxaban inhibits both the "free" and prothombinase-complex-bound forms of activated factor X. Sixty-six percent of orally ingested rivaroxaban is excreted by the kidneys.

In one embodiment, the present invention provides a method of identifying a coagulation inhibitor in a sample, comprising: a) contacting a first portion of the sample with a substrate and thrombin; b) contacting a second portion of the sample with a substrate and a2M-thrombin (thrombin caged in alpha-2-macroglobulin); c) contacting a third portion of the sample with a substrate and coagulation factor Xa; d) contacting a fourth portion of the sample with a substrate and a2M-Xa (factor Xa caged in alpha-2-macroglobulin); and e) assaying for cleavage of the substrate in (a), (b), (c) and (d) above, wherein cleavage of the substrate in (b) and (d) and no cleavage in (a) and (c) identifies heparin in the sample; cleavage of the substrate in (a), (b) and (d) and no cleavage in (c) identifies low molecular weight heparin in the sample; cleavage of the substrate in (a) and (b) and no cleavage in (c) and (d) identifies rivaroxaban in the sample, and cleavage of the substrate in (c) and (d) and no cleavage in (a) and (b)) identifies dabigatran in the sample.

If cleavage is observed in (a), (b), (c) and (d), the assay results can be interpreted to mean that there is no coagulation inhibitor in the sample or that there is a coagulation inhibitor in the sample that is not heparin, low molecular weight heparin, rivaroxaban or dabigatran (e.g., the anticoagulant, warfarin, may be in the sample). If no cleavage is observed in (a), (b), (c) and (d), the assay results can be interpreted to mean that the assay did not work properly or that there may be both rivaroxaban and dabigatran in the sample (Table 1)

In some embodiments, the above method would be carried out using a sample from a subject who does not know or is not able to communicate that he/she has an coagulation inhibitor in his/her body (e.g., the subject is not conscious or otherwise unable to communicate this information). In some embodiments, the subject may be bleeding and normal or routine efforts to control or stop the bleeding are not or have not been effective and/or the subject may need to undergo an emergency surgery and information regarding whether the subject has a coagulation inhibitor in his/her body is not available. The methods of this invention could therefore be carried out on a sample from the subject to determine if there is a coagulation inhibitor in the subject's body and if so, what the coagulation inhibitor is, in order to determine what therapeutic approach to take.

In some embodiments, the methods of this invention can further comprise the step of determining the amount of a coagulation inhibitor in the sample, comprising measuring the amount of cleavage of the substrate in (a), (b), (c) and/or (d) if cleavage was detected, wherein the amount of cleavage of the substrate allows for a determination of the amount of the coagulation inhibitor in the sample. An example of an assay for determining the amount of a coagulation inhibitor in a sample is provided herewith as Example 5.

Quantitation of the amount of a coagulation inhibitor in a sample from a subject allows for a determination of an amount (e.g., a therapeutic amount) of a therapeutic agent of this invention (e.g., a2M-thrombin, a2M-Xa, a2M, a2M-VIIa, a2M-XIa, a2M-plasmin, a2M-kallikrein, a2M-APC, etc.) to be administered to the subject to reduce or inhibit the activity of the coagulation inhibitor in the subject (i.e., to control or stop bleeding). As described herein, the therapeutic goal is to administer a therapeutic agent of this invention in an amount that is greater (e.g., 1% greater, 2% greater, 3% greater, 4% greater, 5% greater, 10% greater, 15% greater, 20% greater, 25% greater, 30% greater, 40% greater, 50% greater, 60% greater, 70% greater, 80% greater, 90% greater, 100% greater, 125% greater, 150% greater, 200% greater, 300% greater, etc.) than the level of the coagulation inhibitor in the subject, in order to reduce, inactivate or inhibit the activity of the coagulation inhibitor in the subject.

Nonlimiting examples of a sample of this invention include a biological sample, such as blood, plasma, serum, urine, feces, lymph tissue, lymph fluid, semen, saliva, tears and/or body fluid, exudate or washing. A sample of this invention can also be a sample not take from a subject, but known to or suspected of containing a coagulation inhibitor, including, e.g., a foodstuff, a beverage, a fluid, an ingestible substance, a forensic sample, etc.

Cleavage of substrate can be detected, for example, as a change in absorbance for a chromogenic substrate or a change in fluorescence for a fluorogenic substrate. Absorbance is measured in a spectrophotometer or microtiter plate reader. Fluorescence is measured in a fluorometer or fluorescence plate reader. Substrate cleavage is converted to enzyme concentration based on a standard curve made with known concentrations of each substance (e.g., thrombin, a2M-thrombin, factor Xa, and a2M-Xa). Dabigatran reduces substrate cleavage by thrombin or a2M-thrombin. The reduced substrate cleavage is converted to a concentration of dabigatran based on a standard curve made using purified dabigatran. Rivaroxaban reduces substrate cleavage by factor Xa or a2M-Xa. The reduced substrate cleavage is converted to a concentration of rivaroxaban based on a standard curve made using purified rivaroxaban.

There are any number of substrates for thrombin and factor Xa and other proteases as described herein that can be used in the methods of this invention. In some embodiments, the substrate is a chromogenic substrate, which can be a para-nitroanalide synthetic substrate. Non-limiting examples of a chromogenic substrate of this invention include tosyl-glycyl-prolyl-arginine para-nitroanilide, H-D-cyclohexylglycyl-alanyl-arginine para-nitroanilide, H-beta-alanyl-glycyl-arginine para-nitroanilide, H-D-cyclohexyl-alanyl-alanyl-arginine para-nitroanilide, H-D-phenylalanyl-pipecolyl-arginine para-nitroanilide, H-D-(carbobenzoyl) lysyl-prolyl-arginine para-nitroanilide, H-beta-alanyl-glycyl-arginine 7-amino-4-methylcoumarin, H-D-cyclohexylglycyl-alanyl-arginine 7-amino-4-methylcoumarin, H-D-(carbobenzoyl)lysyl-prolyl-arginine 7-amino-4-methylcoumarin, methoxycarbonyl-D-cyclohexylalanyl-glycyl-arginine para-nitroanilide, methoxycarbonyl-D-cyclohexylglycyl-glycyl-arginine para-nitroanilide, benzoyloxycarbonyl-D-arginyl-glycyl-arginine para-nitroanilide, benzoyl-isoleucyl-glutamyl-glycyl-arginine para-nitroanilide, methylsulfonyl-D-cyclohexylalanyl-glycyl-arginine 7-amino-4-methylcoumarin, and methoxycarbonyl-D-cyclohexylalanyl-glycyl-arginine 7-amino-4-methylcoumarin. In the examples described herein, the substrate methoxycarbonyl-D-cyclohexylalanyl-glycyl-arginine-para-nitroaniline was used for thrombin, a2M-thrombin, factor Xa, and a2M-Xa.

Non-limiting examples of a fluorogenic substrate that can be used in the methods of this invention include compounds with leaving groups of 7-amino-4-methylcoumarin (AMC), 7 Amido-4-trifluoromethyl coumarin (AFC) and 4-methoxy-β-naphthylamide (4MβNA).

For a chromogenic substrate, such as a para-nitroanilide substrate, cleavage can be measured as a change in absorbance at 405 nm (410 nm can also be used). For a fluorogenic substrate, cleavage can be measured as a change in fluorescence emission at 440-460 nm (excitation 340-380 nm) for AMC, at 495-505 nm (excitation 395 nm) for AFC, or at 410-440 nm (excitation 335-350 nm) for 4MβNA.

In further embodiments, the present invention provides a therapeutic agent and methods of use thereof. Thus, the present invention provides a method of reducing the activity of an oral coagulation inhibitor in the circulation of a subject (e.g., a subject in need thereof, such as a subject who has taken an oral coagulation inhibitor or to whom an oral coagulation has been administered or is believed to have been administered), comprising administering to the subject a therapeutic amount of a therapeutic agent of this invention (e.g., a2M-thrombin if the subject has taken an oral coagulation inhibitor that targets thrombin or a2M-Xa if the subject has taken an oral coagulation inhibitor that targets factor Xa) to reduce, inhibit and/or control the activity of the coagulation inhibitor and/or inactivate the coagulation inhibitor in the subject.

In further embodiments of the present invention, the activity of small molecule inhibitors of factor IXa could be reduced by administering a2M-IXa; the activity of small molecule inhibitors of factor VIIa could be reduced by administering a2M-VIIa; the activity of small molecule inhibitors of factor XIa could be reduced by administering a2M-XIa; the activity of small molecule inhibitors of factor XIIa could be reduced by administering a2M-XIIa; the activity of small molecule inhibitors of activated protein C could be reduced by administering a2M-APC; the activity of small molecule inhibitors of kallekrein could be reduced by administering a2M-kallekrein; and/or the activity of small molecule inhibitors of plasmin could be reduced by administering a2M-plasmin.

A subject of this invention can be any animal to which an oral coagulation inhibitor has been administered or can be administered or is suspected to have been administered or into which a coagulation inhibitor has been introduced or is suspected of having been introduced, either intentionally or nonintentionally. A subject of this invention can also be a subject about which no information is available regarding whether there is a coagulation inhibitor in the body of the subject. In some embodiments, the subject of this invention is a mammal and in some embodiments, the subject of this invention is a human. In some embodiments, the subject is having a surgical procedure or preparing for a surgical procedure. In some embodiments, the subject is having or has had an adverse reaction to an oral coagulation inhibitor and/or is at risk of having an adverse reaction to the oral coagulation inhibitor. In some embodiments, a subject of this invention is a subject for whom control of bleeding is desired and such a subject can be a subject that is not responding to routine or normal efforts to control bleeding. In some embodiments, a subject may not know or may not be able to communicate that he/she has a coagulation inhibitor in his/her body.

In some embodiments of this invention, the a2M-thrombin, a2M-Xa, a2M-IXa, a2M-VIIa, a2M-XIa, a2M-XIIa, a2M-APC, a2M-kallekrein and/or a2M-plasmin can be administered to a subject in a dosage range from about 2 nmol/kg to about 200 nmol/kg. The therapeutic goal is to achieve a plasma level of the a2M-complexed molecule (e.g., a2M-Xa; a2M-IIa, etc., as described herein) in the subject that exceeds the plasma level of the oral coagulation inhibitor being targeted in the subject.

EXAMPLES

Example 1

Complexes of alpha2-macroglobulin (a2M) with thrombin (IIa) and factor Xa were made and studies were conducted that showed that they had the expected properties against the thrombin inhibitor dabigatran and the factor Xa inhibitor rivaroxaban.

A fixed concentration of either a2M-IIa or a2M-Xa in 20 mM HEPES (pH 7.4), 150 mM NaCl was added to the indicated concentration of either dabigatran or rivaroxaban and incubated for 5 minutes. 0.5 mM of para-nitroanilide synthetic substrate (Pefachrome FXa) was added and the rate of substrate cleavage determined by appearance of yellow color characteristic of the cleaved substrate. Pefachrome FXa is also effective as a substrate for thrombin. The rate of substrate cleavage for each complex (a2M-IIa and a2M-Xa) is expressed relative to the rate in the absence of inhibitor.

There is a clinical assay called a thrombin clotting time (TCT) that is done by adding thrombin to plasma. Thrombin clots plasma by binding to fibrinogen and cleaving fibrinopeptides A and B to give fibrin monomer; fibrin monomers aggregate together to give a fibrin clot. As expected, a2M-IIa did not clot plasma. This is because once thrombin is trapped in the a2M "cage" it cannot interact with macromolecular substrates such as fibrinogen.

A fixed concentration of a2M-IIa was added to plasma. The indicated concentration of dabigatran was added and incubated for 5 minutes. One part plasma was added to one part buffer containing 0.5 mM of para-nitroanilide synthetic substrate (Pefachrome FXa) and the rate of substrate cleavage determined by appearance of yellow color characteristic of the cleaved substrate. As cleavage of the substrate was measured kinetically, background absorbance from the plasma did not interfere with the measurement. The rate of substrate cleavage is expressed relative to the rate of substrate cleavage in the absence of dabigatran.

The aPTT (activated partial thromboplastin time) was determined by adding one part normal pooled plasma (unaltered or with dabigatran added) to one part buffer or a2M-IIa in buffer. The mixture was incubated for 3 minutes. One part Kontact aPTT reagent was added and incubated for 3 minutes. The clotting reaction was started by adding one part 25 mM calcium chloride and the time to clot formation was recorded.

Alpha-2-macroglobulin (a2M) was isolated from human plasma as described (van der Graaf et al. "Interaction of human plasma kallikrein and its light chain with alpha-2-macroglobulin" *Biochemistry* 1984; 23:1760-1766 (1984) doi: 10.1021/bi00303a027). Polyethylene glycol was added to give a 4% solution and the precipitate was discarded. Additional polyethylene glycol was added to give a 12% solution; under these conditions a2M was found in the precipitate. The precipitate was resuspended and dialyzed against water. The resulting precipitate was discarded and the solution dialyzed against 20 mM sodium phosphate (pH 6.8), 800 mM sodium chloride. The protein was bound to a metal chelate column that had been equilibrated with zinc chloride. Purified a2M was eluted with a gradient of starting buffer and 100 mM sodium acetate (pH 5.1).

Thrombin (factor IIa) was purchased from Haematologic Technologies. Factor Xa was purchased from Enzyme Research Labs.

Varied concentrations of thrombin and factor Xa were titrated against a2M to determine the ratio of proteins that gave optimal incorporation. Thrombin or factor Xa were incubated with a2M for 2 hours at 37° C., Aliquots of the titrated mixtures were incubated with antithrombin in the presence of heparin. Free thrombin or factor Xa is inactivated by antithrombin/heparin; thrombin or factor Xa in complex with a2M (a2M-IIa or a2M-Xa) are protected from inactivation by antithrombin/heparin.

a2M-IIa, produced at large scale using optimal incubation conditions, was bound to a Q-Sepharose column; free thrombin did not bind to this column. Purified a2M-IIa was eluted from the column with 1M sodium chloride in 20 mM HEPES (pH 7.4).

a2M-Xa, produced at large scale using optimal incubation conditions, was passed through a heparin Sepharose column; free factor Xa bound to the column while the a2M-Xa complex did not. a2M-Xa complex that passed through the heparin column was bound to a Q-Sepharose column and eluted with 1M sodium chloride in 20 mM HEPES (pH 7.4).

The concentrations of thrombin and factor Xa in the a2M-IIa and a2M-Xa complexes, respectively, were estimated from the rate of cleavage of synthetic substrate. The rates of substrate cleavage were converted to concentrations using measured Km and kcat values determined as previously described (Joost et al. "Inhibition of human blood coagulation factor Xa by alpha-2-macroglobulin" *Biochemistry* 26:5932-5937 (1987) doi: 10.1021/bi00392a053) (FIGS. 1-5).

Example 2

Mice were administered 7 μg/kg dabigatran which was designed to produce a plasma level of 65 ng/mL (140 nM). Dabigatran concentration assumes complete recovery and 35% bound to plasma proteins (Stangier and Clemens. "Pharmacology, pharmacokinetics, and pharmacodynamics of dabigatran etexilate, an oral direct thrombin inhibitor" *Clin Appl Thromb Hemost.* 15 Suppl 1:9S-16S (2009) doi: 10.1177/1076029609343004). The peak plasma level of dabigatran in healthy human volunteers was 150 ng/mL (van Ryn et al. "Dabigatran etexilate—a novel, reversible, oral direct thrombin inhibitor: interpretation of coagulation assays and reversal of anticoagulant activity" *Thromb Haemost.* 103:1116-1127 (2010) doi:10.1160/TH09-11-0758).

Figure 6:
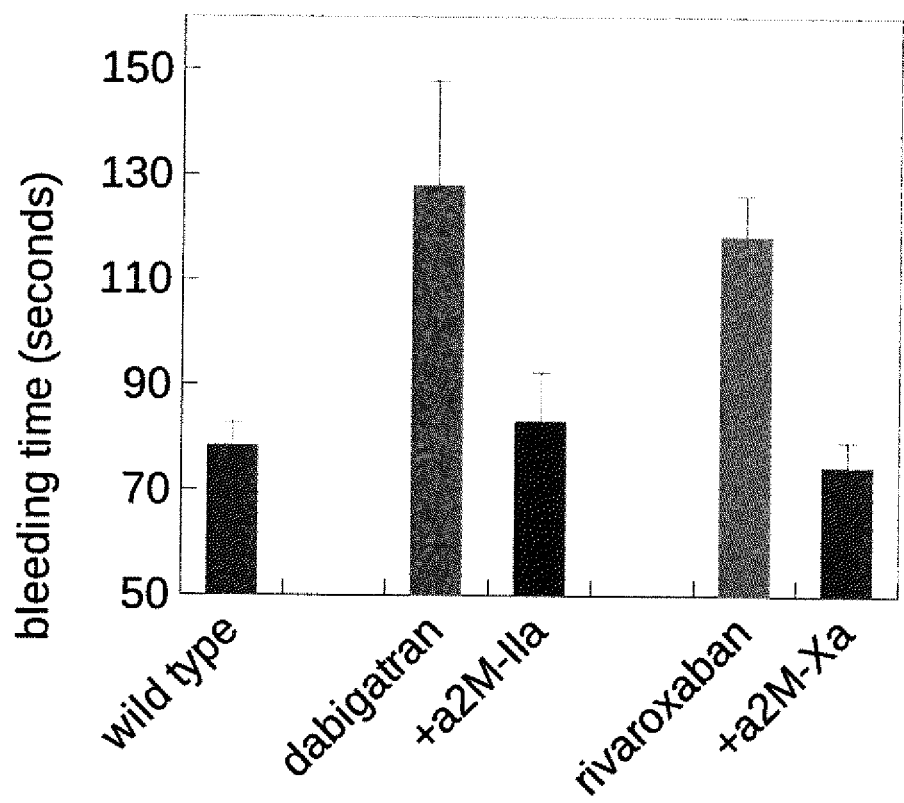
FIG. 6. In normal mice, an injury to the saphenous vein in the leg will stop bleeding in just over 1 minute. Administration of dabigatran to a normal mouse prolongs bleeding such that the same injury requires more than 2 minutes to stop bleeding. Administration of dabigatran followed by administration of a2M-IIa restores the normal bleeding time of a little over 1 minute. Similarly, administration of rivaroxaban to a normal mouse prolongs bleeding such that the same injury requires almost 2 minutes to stop bleeding. Administration of rivaroxaban followed by administration of a2M-Xa restores the normal bleeding time of about 1 minute.

To reverse the effects of this dose of dabigatran, mice were also given 8 nmol/kg a2M-IIa, designed to produce a plasma level of 115 nM (FIG. 6).

Example 3

Mice were administered 160 μg/kg rivaroxaban designed to produce a free plasma level of 36 ng/mL (75 nM), assuming 1.6% recovery based on estimates from Gnoth et al. ("in vitro and in vivo P-glycoprotein transport characteristics of rivaroxaban" *J Pharmacol Exp Thor.* 338:372-380 (2011) doi: 10.1124/jpet.111.180240) and Weinz et al. ("Pharmacokinetics of BAY 59-7939—an oral, direct Factor Xa inhibitor—in rats and dogs" *Xenobiotica* 35:891-910 (2005) doi: 10.1080/00498250500250493) and accounting for 95-98% blood cell and plasma protein binding (Weinz et al. "Pharmacokinetics of BAY 59-7939—an oral, direct Factor Xa inhibitor—in rats and dogs" *Xenobiotica* 35:891-910 (2005))

To reverse the effects of this dose of rivaroxaban, mice were also given 2.3 nmol/kg a2M-Xa, designed to produce a plasma level of 50 nM.

Example 4

Mice were fed Xarelto or Pradaxa or regular chow. Plasma from the animals was analyzed for the presence of dabigatran (active metabolite of Pradaxa) or rivaroxaban (active component of Xarelto). A fixed concentration of plasma was added to a fixed concentration of a2M-IIa or a2M-Xa and incubated for 5 minutes. 0.5 mM of para-nitroanilide synthetic substrate (Pefachrome FXa) was added and substrate cleavage was determined by appearance of yellow color characteristic of the cleaved substrate. Dabigatran in plasma blocked a2M-IIa cleavage of substrate but had no effect on a2M-Xa cleavage of substrate. Rivaroxaban in plasma blocked a2M-Xa cleavage of substrate but had no effect on a2M-IIa cleavage of substrate. In plasma from animals fed regular chow (i.e., containing neither dabigatran nor rivaroxaban), both a2M-IIa and a2M-Xa could cleave substrate (Table 2).

Example 5

For dabigatran, we were able to compare the quantitation of our assay against a clotting assay (activated partial thromboplastin time (aPTT)). This assay is not a standard clinical assay for dabigatran but it can be used in the research setting. As a control, we used plasma calibrated against the international reference standard.

Figure 7:
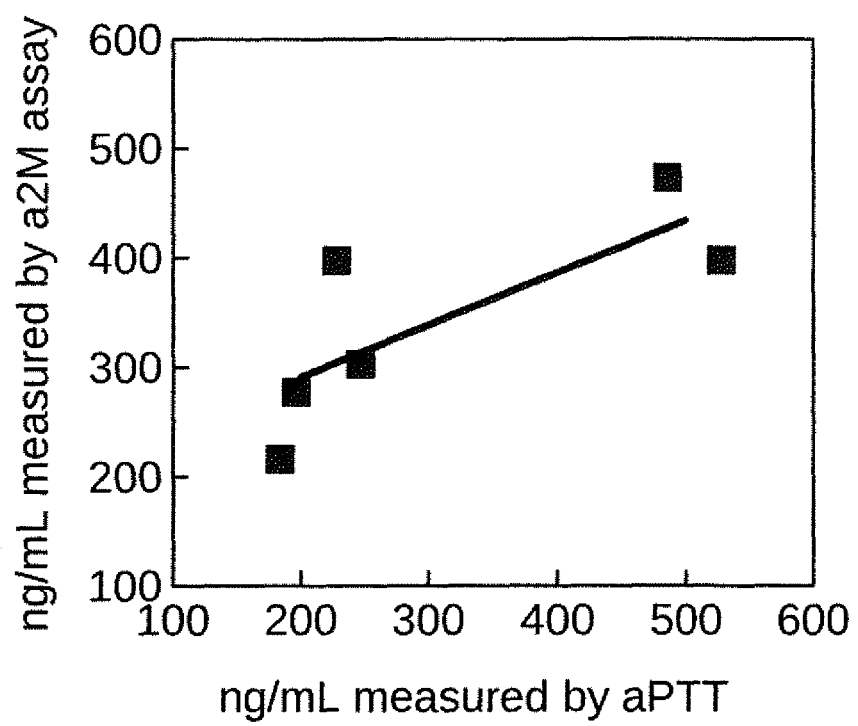
FIG. 7. Comparison of two assays for quantitation of dabigatran in the plasma of mice that were fed Pradaxa.

Plasma from mice fed Pradaxa was assayed to determine the levels of dabigatran in the plasma. Two assays were done on the plasma. For the aPTT, one part plasma was added to one part Kontact aPTT reagent and incubated for 3 minutes. The clotting reaction was started by adding one part 25 mM calcium chloride and the time to clot formation was recorded. Dabigatran blocked thrombin formed in the clotting reaction and prolonged the aPTT. The clotting times were converted into a concentration of dabigatran based on a standard curve made with International Reference Standard plasma. For the a2M-IIa assay, a fixed concentration of a2M-IIa was added to a fixed concentration of plasma and incubated for 5 minutes. 0.5 mM of para-nitroanilide synthetic substrate (Pefachrome FXa) was added and the rate of substrate cleavage determined by appearance of yellow color characteristic of the cleaved substrate. The rate of synthetic substrate cleavage was converted to a concentration of dabigatran based on a standard curve made with International Reference Standard plasma. The concentration of dabigatran as measured by the aPTT was plotted against the concentration as measured by the a2M-IIa assay (FIG. 7). It is expected that the values obtained in the two assays would agree with each other. The extent of agreement can be compared by statistical test such as the Pearson Correlation. In this test, the r value is 0.77, indicating strong agreement between the tests.

The foregoing is illustrative of the present invention, and is not to be construed as limiting thereof. The invention is defined by the following claims, with equivalents of the claims to be included therein.

All publications, patent applications, patents, patent publications and other references cited herein are incorporated by reference in their entireties for the teachings relevant to the sentence and/or paragraph in which the reference is presented.

TABLE 1

| | (a) Thrombin | (b) a2M-thrombin (a2M-IIa) | (c) Factor Xa | (d) a2M-Xa |
|---|---|---|---|---|
| Heparin in sample | No Cleavage | Cleavage | No Cleavage | Cleavage |
| Low molecular weight heparin in sample | Cleavage | Cleavage | No Cleavage | Cleavage |
| Rivaroxaban in sample | Cleavage | Cleavage | No Cleavage | No Cleavage |
| Dabigatran in sample | No Cleavage | No Cleavage | Cleavage | Cleavage |
| No anti-coagulant in sample or Warfarin possibly in sample | Cleavage | Cleavage | Cleavage | Cleavage |
| Assay error or both Rivaroxaban and Dabigatran in sample | No Cleavage | No Cleavage | No Cleavage | No Cleavage |

TABLE 2

| Animal | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Fed Xarelto | + | + | + | + | + | + | | | | | | | | | | |
| Fed Pradaxa | | | | | | | + | + | + | + | + | + | | | | |
| Fed chow | | | | | | | | | | | | | + | + | + | + |
| Dabigatran | no | no | no | no | no | no | yes | yes | yes | yes | yes | yes | no | no | no | no |
| Rivaroxaban | yes | yes | yes | yes | yes | yes | no | no | no | no | no | no | no | no | no | no |

That which is claimed is:

1. A method of identifying a coagulation inhibitor in a liquid sample, comprising:
  a) contacting a first portion of the liquid sample with thrombin and a substrate cleavable by thrombin;
  b) contacting a second portion of the liquid sample with a2M-thrombin and a substrate cleavable by a2M-thrombin;
  c) contacting a third portion of the liquid sample with coagulation factor Xa and a substrate cleavable by coagulation factor Xa;
  d) contacting a fourth portion of the liquid sample with a2M-coagulation factor Xa and a substrate cleavable by a2M-coagulation factor Xa; and
  e) assaying for cleavage of the substrate[s] in (a), (b), (c) and (d) above,
  wherein cleavage of the substrate[s] in (b) and (d) and no cleavage in (a) and (c) identifies heparin in the sample;
  cleavage of the substrate[s] in (a), (b) and (d) and no cleavage in (c) identifies low molecular weight heparin in the sample;
  cleavage of the substrate[s] in (a) and (b) and no cleavage in (c) and (d) identifies rivaroxaban in the sample, and cleavage of the substrate[s] in (c) and (d) and no cleavage in (a) and (b) identifies dabigatran in the sample.

2. The method of claim 1, further comprising the step of determining the amount of the coagulation inhibitor in the liquid sample, comprising measuring the amount of cleavage of the substrate[s] in (a), (b), (c) and/or (d) if cleavage was detected, wherein the amount of cleavage of the substrate determines the amount of the coagulation inhibitor in the sample.

\* \* \* \* \*